United States Patent [19]

Loose et al.

[11] Patent Number: 5,545,656
[45] Date of Patent: Aug. 13, 1996

US005545656A

[54] 2-OXINDOLE-1-CARBOXAMIDE PHARMACEUTICAL AGENTS FOR THE TREATMENT OF ALZHEIMER'S DISEASE

[75] Inventors: Leland D. Loose, Norwich; Joseph G. Lombardino, Niantic; Ethan S. Weiner, East Lyme, all of Conn.

[73] Assignee: Pfizer Inc., New York, N.Y.

[21] Appl. No.: 417,178

[22] Filed: Apr. 5, 1995

[51] Int. Cl.⁶ .................. A61K 31/40; A61K 31/495; A61K 31/505; A61K 31/44; A61K 31/41; A61K 31/425; A61K 31/42; A61K 31/415

[52] U.S. Cl. .................. 514/414; 514/253; 514/256; 514/333; 514/339; 514/361; 514/362; 514/363; 514/365; 514/372; 514/374; 514/378; 514/397; 514/406; 514/411; 514/418; 544/405

[58] Field of Search ..................... 514/414, 253, 514/256, 333, 339, 361, 362, 363, 365, 372, 374, 378, 397, 406, 411, 418

[56] References Cited

U.S. PATENT DOCUMENTS

| | | |
|---|---|---|
| 4,556,672 | 12/1985 | Kadin ..................... 514/414 |
| 4,853,409 | 8/1989 | Showell ..................... 514/418 |
| 4,861,794 | 8/1989 | Otterness ..................... 514/414 |
| 5,006,547 | 4/1991 | Loose ..................... 514/414 |
| 5,008,283 | 4/1991 | Blackburn ..................... 514/414 |
| 5,122,534 | 6/1992 | Loose ..................... 514/414 |
| 5,290,802 | 3/1994 | Ehrgott ..................... 514/414 |

FOREIGN PATENT DOCUMENTS

WO95/00091  2/1995  WIPO.

OTHER PUBLICATIONS

McGeer et al., *Neurology*, 42, 447–9, (1992).
Rogers et al., *Neurology*, 43, 1609–11, (1993).

*Primary Examiner*—Theodore J. Criares
*Attorney, Agent, or Firm*—Peter C. Richardson; Paul H. Ginsburg; Karen DeBenedicts

[57] ABSTRACT

This invention relates to the use of certain 3-substituted 2-oxindole-1-carboxamides and their pharmaceutically acceptable base salts for the treatment or prevention of Alzheimer's disease in mammals, including humans.

12 Claims, No Drawings

2-OXIDOLE-1-CARBOXAMIDE PHARMACEUTICAL AGENTS FOR THE TREATMENT OF ALZHEIMER'S DISEASE

This invention relates to the use of certain 3-substituted-2-oxindole-1-carboxamides and their pharmaceutically acceptable base salts for the treatment and prevention of Alzheimer's disease in mammals, including humans.

Tenidap (5-chloro-2,3-dihydro-2-oxo-3-(2-thienylcarbonyl)-indole-1-carboxamide), has the structural formula

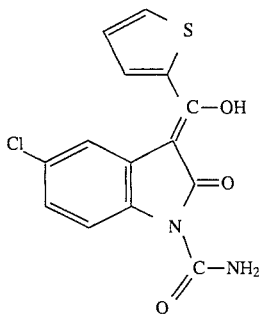

Tenidap and other 3-substituted-2-oxindole-1-carboxamides are referred to in U.S. Pat. No. 4,556,672, which issued on Dec. 3, 1985. This patent refers to the use of such compounds as antiinflammatory and analgesic agents, and as inhibitors of both the cyclooxygenase (CO) and lipoxygenase (LO) enzymes. This patent is incorporated herein by reference in its entirety.

Other 3-substituted-2-oxindole derivatives are referred to in U.S. patent application No. 07/340,113, which was filed on Apr. 18, 1989 and has since been abandoned, and in U.S. Pat. No. 5,290,802, which issued on Mar. 1, 1994. Both these documents are incorporated herein by reference in their entities.

U.S. Pat. No. 4,861,794, which issued on Aug. 29, 1989, refers to the use of tenidap and certain other 3-substituted-2-oxindole-1-carboxamides to inhibit interleukin-1 biosynthesis in mammals and to treat interleukin-1 mediated disorders and dysfunctions. This patent is incorporated herein by reference in its entirety.

U.S. Pat. No. 4,853,409, which issued on Aug. 1, 1989, refers to the use of tenidap and certain other 3-substituted-2-oxindole-1-carboxamides to suppress T-cell function in mammals and to treat T-cell mediated autoimmune disorders of the systemic or organ specific type. This patent is incorporated herein by reference in its entirety.

European Patent 277,738, which issued on Mar. 18, 1992, refers to an anhydrous, crystalline form of the sodium salt of tenidap. This patent is incorporated herein by reference in its entirety.

U.S. Pat. No. 5,008,283, which issued on Apr. 16, 1991, refers to the use of tenidap and its pharmaceutically acceptable base salts to inhibit activation of collagenase, treat collagenase mediated disorders and diseases and inhibit the activity of myeloperoxidase in mammals. This patent is incorporated herein by reference in its entirety.

U.S. Pat. No. 5,006,547, which issued on Apr. 9, 1991, refers to the use of tenidap and its pharmaceutically acceptable base salts to inhibit the release of elastase by neutrophils in mammals and to treat elastase mediated diseases and dysfunctions in mammals. This patent is incorporated herein by reference in its entirety.

U.S. Pat. No. 5,122,534, which issued on Jun. 16, 1992, refers to the use of tenidap and its pharmaceutically acceptable base salts to reduce total serum cholesterol, LDL cholesterol and triglycerides in mammals. This patent is incorporated herein by reference in its entirety.

U.S. patent application No. 08/204,844, filed Mar. 2, 1994, and World Patent Application PCT/IB 95/00091, which designates the United States and was filed on Feb. 10, 1995, refers to the use of tenidap and other 2-oxindole-1-carboxamide derivatives for the treatment of ischemia induced myocardial injury and cytokine mediated myocardial injury.

The 2-oxindole-1-carboxamide derivatives referred to below as "compounds of the formula I", which include tenidap, are also believed to be useful in the treatment and prevention of Alzheimer's disease and the symptoms of such disease such as memory impairment and Alzheimer's dementia. It has been suggested that antiinflammatory agents used in rheumatoid arthritis, specifically nonsteroidal anti-inflammatory drugs (NSAIDs), be studied in this context. The present inventors believe that tenidap, with its combination of cyclooxygenase inhibiting properties and cytokine modulating properties, would be uniquely suited for the treatment of Alzheimer's disease. Tenidap's modulation of cytokine production and acute phase proteins is expected to exert an effect on central nervous system ("CNS") immune activation and to therefore have a more fundamental effect on slowing plaque formation and neuronal damage, and hence on the progression of Alzheimer's disease, than simple NSAIDs, with which tenidap shares properties as a cyclooxygenase inhibitor.

This invention relates to a method of treating or preventing Alzheimer's disease in a mammal, including a human, comprising administering to said mammal an amount of a compound having the formula

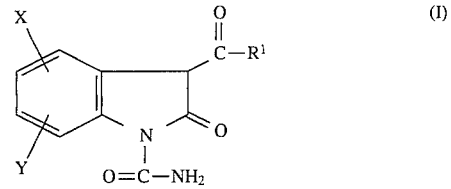

wherein X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls;

Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y, when taken together, are a 4,5-, 5,6- or 6,7-methylenedioxy group or a 4,5-, 5,6- or 6,7-ethylenedioxy group;

or X and Y, when taken together and attached to adjacent carbon atoms, form a divalent radical Z, wherein Z is selected from the group consisting of

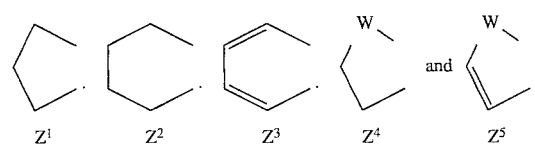

wherein W is oxygen or sulfur;

$R^1$ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo[2.2.1]heptan-2-yl, bicyclo[2.2.1]hept-5-en-2-yl and —$(CH_2)_n$—Q—$R^o$;

and wherein there are 1 or 2 substituents on said substituted phenyl, said (substituted phenyl)alkyl and said (substituted phenoxy)alkyl, said substituents being independently selected from the group consisting of fluoro, chloro, bromo, alkyl having 1 to 4 carbons, alkoxy having 1 to 4 carbons and trifluoromethyl;

n is zero, 1 or 2;

Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]thiophene;

$R^o$ is hydrogen, chloro, fluoro, bromo or alkyl having 1 to 3 carbons;

or a pharmaceutically acceptable salt of such compound, or a solvate (e.g., a hemihydrate or monohydrate) of such compound or salt, that is effective in treating or preventing such condition.

Compounds of the formula I, while depicted above in their "keto" tautomeric form, can also exist in their corresponding "enol" tautomeric form. Also, compounds of the formula I may contain chiral centers and therefore may exist in different enantiomeric forms. This invention includes methods of treating or preventing Alzheimer's disease, as defined above, that employ compounds of the formula I in one or both of their tautomeric forms. It also includes such methods that employ compounds of the formula I in their racemic or any of their stereoisomeric forms.

This invention also relates to methods of treating or preventing Alzheimer's disease that employ a prodrug of a compound of the formula I. The term "prodrug", as used herein, refers to compounds that are drug precursors which, following administration to and absorption by a mammal, release the drug in vivo via a metabolic process.

A preferred embodiment of this invention relates to the above method of treating or preventing Alzheimer's disease wherein the compound administered is a compound wherein Y is hydrogen and X is selected from 5-chloro, 6-chloro, 5-fluoro, 6-fluoro, 5-trifluoromethyl and 6-trifluoromethyl, or a pharmaceutically acceptable salt of such compound, or a solvate of such compound or salt.

Another preferred embodiment of this invention relates to the foregoing preferred embodiment wherein, in the compound that is administered, $R^1$ is selected from benzyl, 2-furyl, 2-thienyl, 2-(4-chloro)thienyl, (2-furyl)methyl and (2-thienyl)methyl.

Another preferred embodiment of this invention relates to the above method of treating or preventing Alzheimer's disease wherein the compound administered is a compound wherein X is selected from 5-chloro and 5-fluoro, and Y is selected from 6-chloro and 6-fluoro, or a pharmaceutically acceptable salt of such compound, or a solvate of such compound or salt.

Another preferred embodiment of this invention relates to the foregoing preferred embodiment wherein, in the compound that is administered, $R^1$ is selected from benzyl, 2-furyl, 2-thienyl, 2-(4-chloro)thienyl, (2-furyl)methyl and (2-thienyl)methyl.

Another preferred embodiment of this invention relates to the above method of treating or preventing Alzheimer's disease wherein the compound of formula I that is administered is selected from the group consisting of:

5-chloro-3-(2-thenoyl)-2-oxindole-1-carboxamide;

5-trifluoromethyl-3-(2-[2-thienyl]acetyl)-2-oxindole-1-carboxamide;

6-fluoro-3-(2-phenylacetyl)-2-oxindole-1-carboxamide;

6-chloro-5-fluoro-3-( 2-phenylacetyl)-2-oxindole-1-carboxamide;

5,6-difluoro-3-(2-furoyl)-2-oxindole-1-carboxamide;

5,6-difluoro-3-(2-thenoyl)-2-oxindole-1-carboxamide;

6-chloro-5-fluoro-3-(2 -thienyl)-2-oxindole-1-carboxamide;

6-chloro-5-fluoro-3-[2-(3-chloro )thienyl]-2-oxindole-1-carboxamide;

5-chloro-3-[2-(3-chloro )thienyl]-2-oxindole-1-carboxamide;

and the pharmaceutically acceptable salts of the foregoing compounds and the solvates of such compounds and salts.

An especially preferred embodiment of this invention relates to the above method of treating or preventing Alzheimer's disease wherein the compound administered is tenidap, a pharmaceutically acceptable salt of tenidap, a solvate of tenidap or a solvate of a pharmaceutically acceptable salt of tenidap.

Compounds of the formula I and their pharmaceutically acceptable base salts, solvates and prodrugs may be prepared as described in U.S. Pat. No. 4,556,672, referred to above.

Compounds of the formula I are acidic and therefore form base salts. Such base salts can be formed as described in U.S. Pat. No. 4,556,672, referred to above. Such salts, within the scope of this invention, include both the organic and inorganic types and include, but are not limited to, the salts formed with ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of bases that form such base salts include ammonia, primary amines such as n-propylamine, n-butylamine, aniline, cyclohexylamine, benzylamine, p-toluidine, ethanolamine and glucamine; secondary amines such as diethylamine, diethanolamine, N-methylglucamine, N-methylaniline, morpholine, pyrrolidine and piperidine; tertiary amines such as triethylamine, triethanolamine, N,N-dimethylaniline, N-ethylpiperidine and N-methylmorpholine; hydroxides such as sodium hydroxide; alkoxides such as sodium ethoxide and potassium methoxide; hydrides such as calcium hydride and sodium hydride; and carbonates such as potassium carbonate and sodium carbonate. Preferred salts are those of sodium, potassium, ammonium, ethanolamine, diethanolamine and triethanolamine. Particularly preferred are the sodium salts.

An anhydrous crystalline form of such a sodium salt of tenidap is referred to in European Patent 277,738, mentioned above.

The methods of this invention comprise administering compounds of the formula I and their pharmaceutically acceptable base salts and solvates of such compounds and salts (hereinafter collectively referred to as "the therapeutic agents") to a mammal. The therapeutic agents can be administered to said mammal either alone or, preferably, in combination with pharmaceutically acceptable carriers or diluents in a pharmaceutical composition, according to standard pharmaceutical practice. Such administration can be accomplished via a variety of routes, including oral, parenteral, rectal and topical. Parenteral administration, as used herein, includes but is not limited to intravenous, intramuscular, intraperitoneal, subcutaneous, and transdermal administration. It is generally preferred to administer the therapeutic agents orally.

For use in the treatment or prevention of Alzheimer's disease, the therapeutic agents are most desirably administered, in accordance with this invention, in doses ranging from about 5 mg to about 250 mg per day, preferably from about 20 mg to about 120 mg per day, in single or divided doses, although variations will necessarily occur depending upon the weight of the subject being treated, the nature and severity of the subject's condition, the potency of the particular compound being administered and the duration of the treatment.

In some instances, dosage levels below the lower limit of the above dosage ranges may be more than adequate, while in other cases still larger dosages may be employed without causing any harmful or deleterious side effects to occur, provided that such higher dosage levels are first divided into several smaller doses that are to be administered throughout the day.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard filled gelatin capsules. Preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerine and various like combinations thereof.

For purposes of parenteral administration, solutions of a therapeutic agent in sesame or peanut oil or in aqueous propylene glycol may be employed, as well as sterile aqueous solutions of the corresponding water soluble base salts previously enumerated. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous-earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these injection solutions to insure that the final products are obtained in a sterile condition.

For purposes of transdermal administration, the dosage form of a particular therapeutic agent may include, by way of example, solutions, lotions, ointments, creams, gels, suppositories, rate limiting sustained release formulations and devices. Such dosage forms comprise the particular compound and may include ethanol, water, penetration enhancers and inert carriers such as gel producing materials, mineral oil, emulsifying agents, benzyl alcohol and the like. Specific transdermalflux enhancing compositions are disclosed in European Patent Applications 271,983 and 331,382, which were published, respectively, on Jun. 22, 1988 and Sep. 6, 1989. These applications are incorporated herein by reference in their entireties.

For purposes of topical administration, the dosage form of a particular therapeutic agent may include, by way of example and not of limitation, solutions, patches, lotions, ointments, creams and gels.

The ability of tenidap and the other compounds of formula I to inhibit the production of $PGD^2$ (a cyclooxygenase pathway) by RBL-1 cells and the release of IL-1β by human monocytes isolated from Ficoll-Hypaque centrifugation of heparinized blood may be determined, respectively, as described in the following protocols.

METHOD FOR ASSESSING THE INHIBITION OF THE CYCLOOXYGENASE PATHWAY IN RAT BASOPHILLIC LEUKEMIA (RBL) CELLS a) RBL-1 cell incubations. RBL-1 cells, maintained in monolayer, were grown for 1 day in spinner culture using Eagle's Minimum Essential Medium with Earle's Salts (JRH Bioscience) plus 15% Fetal Bovine Serum (GIBCO) supplemented with antibiotic/antimycotic solution (GIBCO) according to the method of Jakschik et al., (1980), Nature, London 287, 51. Briefly, the cells were washed 3X with RPMI 1640 (GIBCO) and resuspended in RPMI 1640 at a cell density of $2 \times 10^6$ cells/ml. A 0.5 ml aliquot of cell suspension was preincubated at 30° C. for 10 minutes with 1 μl dimethyl sulfoxide (DMSO) solution of drug. The incubation was started by simultaneous addition of 5 μl [$^{14}$C]-arachidonic acid (specific radioactivity, 50–55 mCi/mmol) dissolved in ethanol and 2 μl calcium ionophore dissolved in DMSO to give final concentrations of 5 and 7.6 μM, respectively. Five minutes later, the incubation was terminated by the addition of a 0.27 ml volume of acetonitrile (ACN)/acetic acid (HOAc) (100:3). The mixture was then clarified of precipitated protein by centrifugation. Analysis of 5-LO/COX pathway products was performed by radioactivity monitoring after separation by high performance liquid chromatography (HPLC). A 100 μl volume of clarified sample was injected ont a Perkin Elmer CRC18 column (3μ, 0.46×3.0 cm) pre-equilibrated with $ACN:H_2O:TFA$ (35:65:0.1). The column was developed using a linear gradient from 35–75% ACN (containing 0.1% TFA) over 8 min at a flow rate of 2 ml/min. The column was held at 75% ACN for an additional 2 minutes before being recycled to original conditions. Detection of product radioactivity was performed with the aid of a Berthold 504 (Radioactivity Monitor equipped with an 200 μl flow cell mixing 2.4 ml/min OMNIFLUOR (New England Nuclear) with column effluent. Integration of peak areas was accomplished by a SP-4200 computing integrator (Spectra Physics). The radio-labeled product profile contained four major peaks. In order of elution, they were prostaglandin $D_2$ ($PGD_2$), dihydroxy fatty acids (DiHETEs), 5-HETE (5-hydroxyeicosatetraenoic acid), and arachidonic acid. DiHETEs including $LTB_4$ (leukotriene B4) are likely derived from $LTA_4$ (leukotriene A4) through enzymic and nonenzymic hydrolysis. The area under the curve (AUC) as measured in integration units for each product was compared to the average AUC value for untreated (no drug) controls. The results for prostaglandin $D_2$ formation were expressed as "Percent of Control" and were plotted versus the log of drug concentration. Half-maximal ($IC_{50}$) points were estimated from these curves.

PROTOCOL FOR ATP-INDUCED IL-Iβ POSTTRANSLATIONAL PROCESSING

Cells: Human monocytes were isolated by Ficoll-Hypaque centrifugation of heparinized blood. The monocyte band off the gradient was collected, diluted with RPMI 1640, 5% fetal bovine serum (FBS), 20 mM N-[2[hydroxyethyl] piperazine-N-[2-ethanesulfonic acid] (Hepes), pH 7.3 (40 ml) and the cells were collected by centrifugation. The cell pellet was washed twice with 30 ml of RPMI 1640, 5% FBS, 20 mM Hepes (Maintenance Medium). The monocytes were resuspended in 50 ml of the Maintenance Medium. Into each well of a 96 well plate was added $2.4 \times 10^5$ mononuclear cells. The cell suspension was diluted to a final concentration of $1.5 \times 10^5$ mononuclear cells. (To accomplish this, the cell suspension was diluted to a final concentration of $1.5 \times 10^6$ cell/ml and 0.2 ml was added to each well of the plate.) After incubating at 37° C. for 2 hours, the supernatant containing non-adherent cells was removed by aspiration. The adherent cells were washed once with 0.15 ml of Maintenance medium. Then, 0.15 ml of fresh Maintenance Medium was added and the cells were incubated overnight at 37° C.

Stimulation: Lipopolysaccharide (LPS) was added to a final concentration of 10 ng/ml and incubated at 37° C. for 2 hours. The medium was replaced with 0.1 ml of RPMI 1640, pH 6.9, 25 mM Hepes, 1% FBS which contained, where indicated, 10 ng/ml LPS, and the indicated concentration of test agent. After a 15 min incubation, the wells that were to be treated with ATP received 10 μl of a 20 mM ATP stock solution (pH 7 in Dulbecco's culture medium). Incubation occurred for an additional 3 hours at 37° C.

ELISA Assay for IL-1β (Kit from R and D systems, Minneapolis, Minn.): Into each well of the ELISA kit was added 0.14 ml of Maintenance Medium. Then 0.06 ml of each of the supernatants from the ATP-kick assay was added and the following instructions were followed.

1. Incubate the ELISA plate at room temperature (RT) for 2 hours to allow capture of IL-1β by the antibody attached to the bottom of the plate.

2. After the 2 hour incubation, aspirate off the supernatant and rinse each well 3X with 0.4 ml of Wash Buffer (supplied with the kit).

3. Add 0.2 ml of the secondary antibody conjugate (with horseradish peroxidase). Incubate at RT for 60 minutes.

4. Aspirate off supernatant and rinse each well 3X with Wash buffer (0.4 ml/wash).

5. Add 0.2 ml of Substrate Solution (Supplied with kit). Incubate at room temperature for 20 minutes.

6. Add 0.05 ml of Stop Solution (Supplied with kit).

7. Determine optical density ($OD_{450}$) within 30 minutes of stop solution addition.

Table 1 below lists $IC_{50}$ values for selected compounds of the formula I that were determined using the methods described above.

TABLE 1

Inhibition of Selected Oxindoles on the Production of $PGD_2$ (cyclooxygenase pathway) by RBL-1 cells and on IL-1β release by HPBM

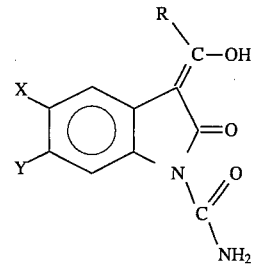

| X | Y | $R^1$ | RBL-cells $PGD_2$ formation $IC_{50} \pm SD$ (N) [μM] | Human Monocyte AtP kick $IC_{50}$ (No. Trials) |
|---|---|---|---|---|
| Cl | H | 2'-thienyl | 0.02 ± 0.02 (8) | 40 μM* (3) |
| F | H | 2'-thienyl | 0.02 ± 0.02 (7) | 66 μM* (1) |
|   |   |   |   | 33 μM (1) |
| F | H | 2'-thienyl | 2.0 (1) | 8% Inh. at 19 μM (1) |
| $CH_3$ | H | 2'-thienyl | 99 (1) | 32% Inh. at 19 μM (1) |
| Cl | H | 3'-thienyl | 0.7 (2) | 14% Inh. at 19 μM (1) |
| Cl | H | 3'-furyl | 3.2 (1) | Not tested |
| Cl | H | benzyl-methyl | 7.3 (1) | Not tested |
| Cl | H | Trifluoromethyl | 37 (1) | Not tested |

*Values for tenidap (the first compound in the table), and in one case ilonidap (the second compound in the table) were derived from a slightly different assay that employed metabolically labeled cells.

We claim:

1. A method of treating or preventing Alzheimer's disease in a patient in need thereof comprising administering to said mammal an amount of a compound of the formula

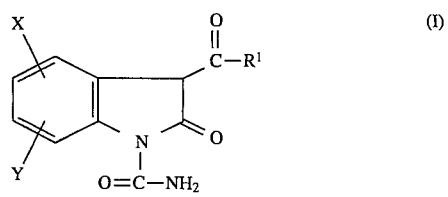

wherein X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfonyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls;

Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y, when taken together, are a 4,5-, 5,6- or 6,7-methylenedioxy group or a 4,5-, 5,6- or 6,7-ethylenedioxy group;

or X and Y, when taken together and attached to adjacent carbon atoms, form a divalent radical Z, wherein Z is selected from the group consisting of

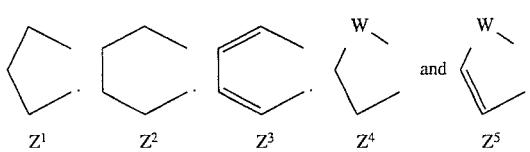

wherein W is oxygen or sulfur;

R¹ is selected from the group consisting of alkyl having 1 to 6 carbons, cycloalkyl having 3 to 7 carbons, cycloalkenyl having 4 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, (thiophenoxy)alkyl having 1 to 3 carbons in said alkyl, naphthyl, bicyclo[2.2.1]heptan-2-yl, bicyclo[2.2.1]hept-5-en-2-yl and —(CH$_2$)$_n$—Q—R$^o$;

and wherein there are 1 or 2 substituents on said substituted phenyl, said (substituted phenyl)alkyl and said (substituted phenoxy)alkyl, said substituents being independently selected from the group consisting of fluoro, chloro, bromo, alkyl having 1 to 4 carbons, alkoxy having 1 to 4 carbons and trifluoromethyl;

n is zero, 1 or 2;

Q is a divalent radical derived from a compound selected from the group consisting of furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b]thiophene;

R$^o$ is hydrogen, chloro, fluoro, bromo or alkyl having to 3 carbons; or a pharmaceutically acceptable salt of such compound, or a solvate of such compound or salt, that is effective in treating or preventing such disease.

2. A method according to claim 1, wherein the compound that is administered is one; wherein Y is hydrogen and X is selected from 5-chloro, 6-chloro, 5-fluoro, 6-fluoro, 5-trifluoromethyl and 6-trifluoromethyl.

3. A method according to claim 2, wherein the compound administered is one wherein R¹ is selected from benzyl, 2-furyl, 2-thienyl, (2-furyl)methyl and (2-thienyl)methyl.

4. A method according to claim 1, wherein the compound administered is one wherein X is selected from 5-chloro and 5-fluoro, and Y is selected from 6-chloro and 6-fluoro.

5. A method according to claim 4, wherein the compound administered is one wherein R¹ is selected from benzyl, 2-furyl, 2-thienyl, (2-furyl)methyl and (2-thienyl)methyl.

6. A method according to claim 1, wherein the compound administered is selected from the group consisting of:

5-chloro-3-(2-thenoyl)-2-oxindole-1-carboxamide;

5-trifluoromethyl-3-(2-[2-thienyl]acetyl)-2-oxindole-1-carboxamide;

6-fluoro-3-(2-phenylacetyl)-2-oxindole-1-carboxamide;

6-chloro-5-fluoro-3-(2-phenylacetyl)-2-oxindole-1-carboxamide;

5,6-difluoro-3-(2-furoyl)-2-oxindole-1-carboxamide;

5,6-difluoro-3-(2-thenoyl)-2-oxindole-1-carboxamide;

6-chloro-5-fluoro-3-(2-thienyl)-2-oxindole-1-carboxamide;

6-chloro-5-fluoro-3-[2-(3-chloro)thienyl]-2-oxindole-1-carboxamide;

5-chloro-3-[2-(3-chloro)thienyl]-2-oxindole-1-carboxamide;

and the pharmaceutically acceptable salts of the foregoing compounds and solvates of such compounds and salts.

7. A method according to claim 1 wherein the compound administered is tenidap, a pharmaceutically acceptable salt of tenidap, a solvate of tenidap or a solvate of a pharmaceutically acceptable salt of tenidap.

8. A method according to claim 7 wherein the sodium salt of tenidap is administered.

9. A method according to claim 7 wherein tenidap, a pharmaceutically acceptable base salt of tenidap, a solvate of tenidap or a solvate of a pharmaceutically acceptable base salt of tenidap is administered orally.

10. A method according to claim 9 wherein the sodium salt of tenidap is administered orally.

11. A method according to claim 7 wherein tenidap, a pharmaceutically acceptable base salt of tenidap, a solvate of tenidap or a solvate of a pharmaceutically acceptable base salt of tenidap is administered parenterally.

12. A method according to claim 11 wherein the sodium salt of tenidap is administered parenterally.

\* \* \* \* \*